(12) United States Patent
Larka et al.

(10) Patent No.: US 9,707,535 B2
(45) Date of Patent: Jul. 18, 2017

(54) MICROFLUIDIC REACTORS FOR OLIGONUCLEOTIDE SYNTHESIS

(71) Applicants: Lance Amate Larka, Huntsville, AL (US); John D. Williams, Decatur, AL (US); Randy Gaillard, Huntsville, AL (US)

(72) Inventors: Lance Amate Larka, Huntsville, AL (US); John D. Williams, Decatur, AL (US); Randy Gaillard, Huntsville, AL (US)

(73) Assignee: The Board of Trustees of the University of Alabama, for and on behalf of the University of Alabama in Huntsville, Huntsville, AL (US)

( * ) Notice: Subject to any disclaimer, the term of this patent is extended or adjusted under 35 U.S.C. 154(b) by 0 days.

(21) Appl. No.: 14/334,497

(22) Filed: Jul. 17, 2014

(65) Prior Publication Data

US 2015/0087820 A1    Mar. 26, 2015

Related U.S. Application Data

(60) Provisional application No. 61/847,397, filed on Jul. 17, 2013.

(51) Int. Cl.
*B01L 3/00*     (2006.01)
*B01J 19/00*    (2006.01)
*C07H 21/00*    (2006.01)

(52) U.S. Cl.
CPC .......... *B01J 19/0093* (2013.01); *C07H 21/00* (2013.01); *B01J 2219/0093* (2013.01); *B01J 2219/00831* (2013.01); *B01L 3/502715* (2013.01)

(58) Field of Classification Search
CPC ............ B01L 3/5027; B01L 3/502715; B01L 3/502761; B01L 2300/0816; B01L 2300/0877; B01L 2400/0418; B01L 2400/0421
USPC .................. 422/502, 504; 436/174, 178, 180
See application file for complete search history.

(56) References Cited

U.S. PATENT DOCUMENTS

| | | | |
|---|---|---|---|
| 5,734,020 A * | 3/1998 | Wong ............................ | 530/350 |
| 6,485,690 B1 * | 11/2002 | Pfost et al. ................... | 422/552 |
| 2004/0018611 A1 * | 1/2004 | Ward et al. ................ | 435/287.2 |
| 2004/0080744 A1 * | 4/2004 | Hobbs ............... | B01L 3/502715 356/246 |

* cited by examiner

*Primary Examiner* — Jill Warden
*Assistant Examiner* — Dwayne K Handy
(74) *Attorney, Agent, or Firm* — Maynard Cooper & Gale, P.C.; Jon E. Holland (57) ABSTRACT

The present disclosure generally pertains to systems and methods for the chemical synthesis of micro-quantities of oligonucleotides or other chemical molecules. The system includes a reusable glass micro-reactor containing a paramagnetic solid support, a magnet, an electronic drive controller and an optical spectroscopy system capable of driving a plurality individual reactors. The system utilizes the electroosmotic movement of reactants through microfluidic channels. Spectrophotometric monitoring of the reaction products allows for the real-time determination of synthesis yield.

23 Claims, 7 Drawing Sheets

FIG. 7 ial Application
MICROFLUIDIC REACTORS FOR OLIGONUCLEOTIDE SYNTHESIS

CROSS REFERENCE TO RELATED APPLICATIONS

This application claims priority to U.S. Provisional Application No. 61/847,397 and filed Jul. 17, 2013, entitled "Microfluidic Reactors for Oligonucleotide Synthesis," which is incorporated herein by reference.

RELATED ART

Oligonucleotide synthesis is the chemical synthesis of relatively short fragments of nucleic acids with a defined sequence. The technique provides a rapid and inexpensive access to custom-made oligonucleotides of the desired sequence. Chemical oligonucleotide synthesis is carried out in the 3' to 5' direction. Currently, the process is implemented as solid-phase synthesis using phosphoramidite method and phosphoramidite building blocks derived from protected 2'-deoxynucleosides (dA, dC, dG, and T), ribonucleosides (A, C, G, and U), or chemically modified nucleosides.

The desired oligonucleotide is obtained by sequentially coupling the building blocks to a growing oligonucleotide chain in the desired order. The product is released from the solid chain assembly, deprotected, and collected. Typically, synthetic oligonucleotides are single-stranded DNA or RNA molecules around 15-25 bases in length, but lengths up to 150 and longer are possible. The oligonucleotide synthesis process is generally completed by the stepwise addition of nucleotide residues to the 5'-terminus of the growing chain until the desired sequence is assembled.

In solid-phase synthesis, an oligonucleotide being assembled is covalently bound, via its 3'-terminal hydroxy group, to the solid support material and remains attached to it over the entire course of the chain assembly. One of the common solid-phase materials is controlled pore glass (CPG). The solid support material is contained in columns whose dimensions depend on the scale of synthesis. At the end of the chain assembly, the oligonucleotide is released from the solid support and is eluted from the column or the well.

Current solid-phase production schemes have been optimized for production of 40,000 pmol up to 1,000,000 pmol (40 nmol to 1 umol respectively) of oligonucleotides per synthesis at high levels of efficiency in terms of quality and reduction in raw material costs. However, the vast majority of end-use processes require a single reaction of 5-10 pmol of product with the remainder being discarded as waste. The demand for sub nanomol scale synthesis has been known for over a decade and various groups have attempted different strategies to reach that level. One such approach is microfluidic synthesis utilizing a three-dimensional (3D) solid support and unique channels. The currently available systems are pressure driven requiring complex valving and filter valves to retain the solid support. The materials used in these efforts were either not compatible with the traditional chemistry, requiring changes that resulted in poor oligonucleotide quality, or are not scalable beyond a single channel due to control purposes. Neither approach allows the synthesis apparatus to be reused, a difficult hurdle when trying to contain costs.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

The present disclosure generally pertains to a glass microreactor system for the synthesis of oligonucleotides. The system includes one or more smooth-walled photodefinable glass substrates which contain a plurality of reactors for oligonucleotide synthesis. The system also utilizes a paramagnetic solid support to drive the synthesis reaction. Electroosmatic pumping reduces the unwanted mixing of reactants. In addition, the system provides for in-plane, real-time optical spectroscopy of synthesis products and closed loop control of analytes and products. The presently disclosed system may be used for the synthesis of DNA, RNA or amino acid strands. For the sake of simplicity, the reference to "oligonucleotide synthesis" will refer to the production of DNA, RNA and amino acid strands.

Figure 1:
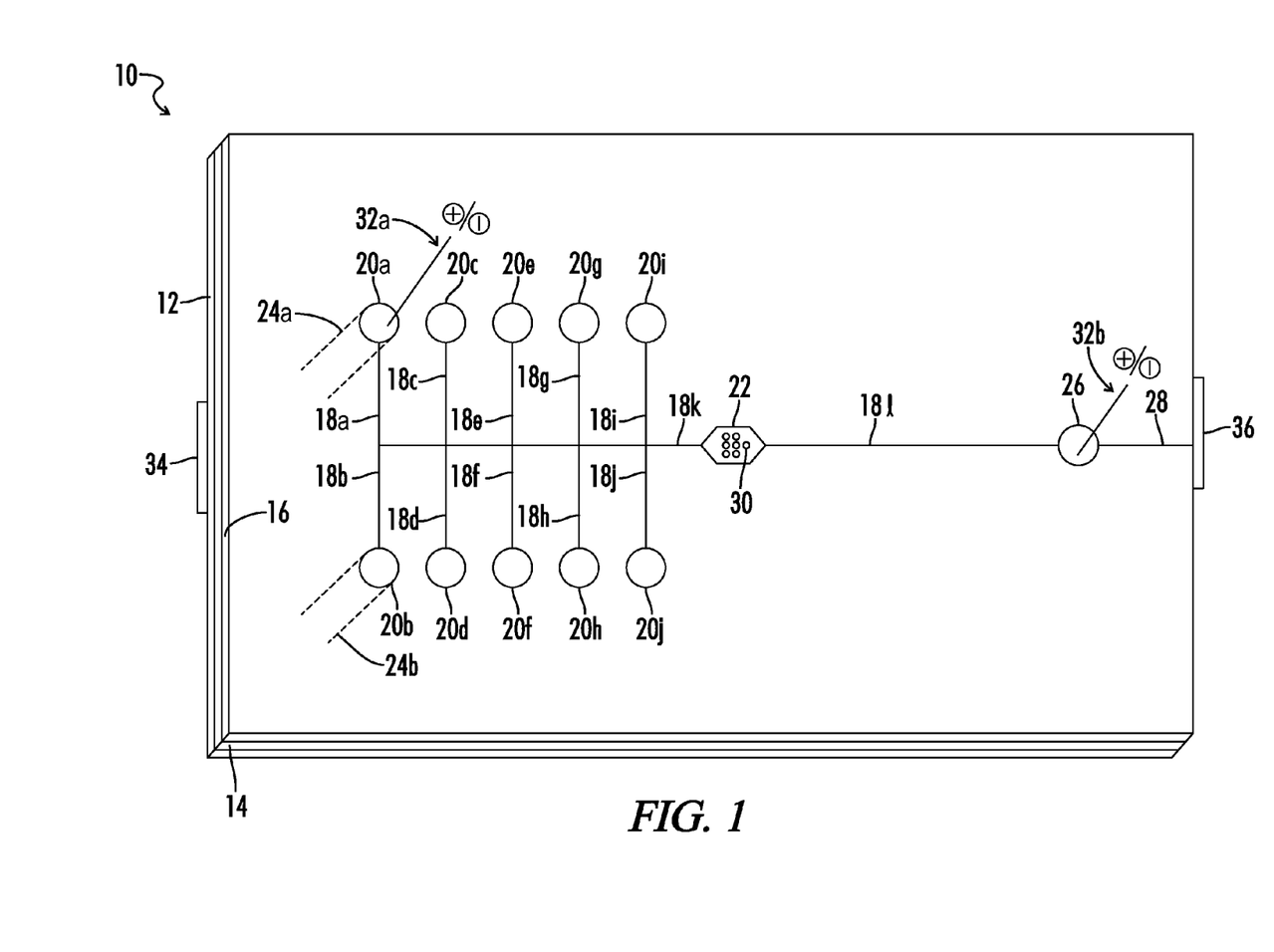
FIG. 1 depicts a front perspective view illustrating an exemplary reaction substrate in accordance with an embodiment of the disclosure.

FIG. 1 illustrates an exemplary embodiment of a reusable glass reactor substrate 10 of the disclosure. In this embodiment, substrate 10 includes three layers 12, 14 and 16 of fully transparent, smooth walled, photodefinable glass. In one embodiment each layer 12, 14 and 16 is approximately 0.5 mm in height, resulting in a substrate with a height of approximately 1.5 mm, although other sizes are possible in other embodiments. The glass used to produce substrate 10 is transparent across the entire visible and near infra-red spectrum and is highly resistant to chemicals used in common oligonucleotide synthesis processes. Current synthesis vessels are often constructed from polydimethylsiloxane (PDMS), which will absorb the synthesis chemicals, swell, and contaminate the product. The glass used to fabricate the substrate 10 prohibits absorption of reactants into the sidewall of the fluid channels 18a-18j or the reagent ports 20a-20j (described in more detail below). Furthermore, the substrate 10 is mechanically, thermally, and chemically stable over a large temperature range, for instance up to 400° C. In one embodiment, substrate 10 is approximately the size of a standard microscope slide (1 in.×3 in.), however other sizes are possible in other embodiments.

Referring to again to the embodiment illustrated in FIG. 1, the first or bottom layer 12 of the glass substrate 10 has a smooth surface and acts to provide structural support to substrate 10. The second or middle layer 14 of the substrate 10 has etched fluid channels 18a-18j. The substrate 10 illustrated in FIG. 1 has ten fluid channels, however other numbers of fluid channels are possible in other embodiments. In one embodiment, the fluid channels 18a-18l are sized at approximately 300 microns×300 microns, although other sizes are possible in other embodiments. Each fluid channel 18a-18l provides fluid communication, for a single synthesis reagent, between the plurality of reagent ports 20a-20j, the reaction chamber 22 and the exit port 26, as will be described in more detail hereinafter. As will be described below, the chemical reactants required for oligonucleotide synthesis travel through fluid channels 18a-18j to the reagent ports 20a-20j and other system components.

The top layer 16 of the glass substrate 10 includes etched reagent ports 20a-20j. Reagent ports 20a-18j allow for the introduction into the substrate 10 of all of the chemical components necessary for oligonucleotid synthesis. Each reagent port 18a-18j includes a tube 24 extending downward through and exiting the bottom layer 12 of the glass substrate 10 to allow for the introduction of reagents from an outside source (not shown). Although FIG. 1 illustrates tubes 24a and 24b (corresponding to reagent ports 20a and 20b), each reagent port 20a-20j will have a corresponding tube 24 to allow for the introduction of liquid analytes.

Referring again to FIG. 1, a reaction chamber 22 is included in the middle layer 14 of substrate 10. Reaction chamber 22 contains the paramagnetic solid support 30 utilized to facilitate the synthesis reaction. The substrate 10 illustrated in FIG. 1 includes one reaction chamber 22. However, a substrate 10 may include multiple reaction chambers 22, for example sixteen reaction chambers 22 per substrate 10. In this embodiment, each reagent port 20a-20j will be in fluid communication with each reaction chamber 22 such that all of the analytes necessary for oligonucleotide synthesis will be available to every reaction chamber 22. In one embodiment, the paramagnetic solid support 30 within the reaction chamber 22 comprises paramagnetic solid support containing a magnetic core. In one example the magnetic core is iron, although the core may be composed of other magnetic substances in other embodiments. The iron core is paramagnetic so that it will be attracted to a magnet (not shown in FIG. 1) placed on the outside of substrate 10, as will be discussed in more detail hereinafter. The substrate 10 further includes an exit port 26 and an exit channel 28 where reagents may exit the substrate 10 for either a waste container (not shown) or for further analysis, as will be described in more detail herein.

Figure 2:
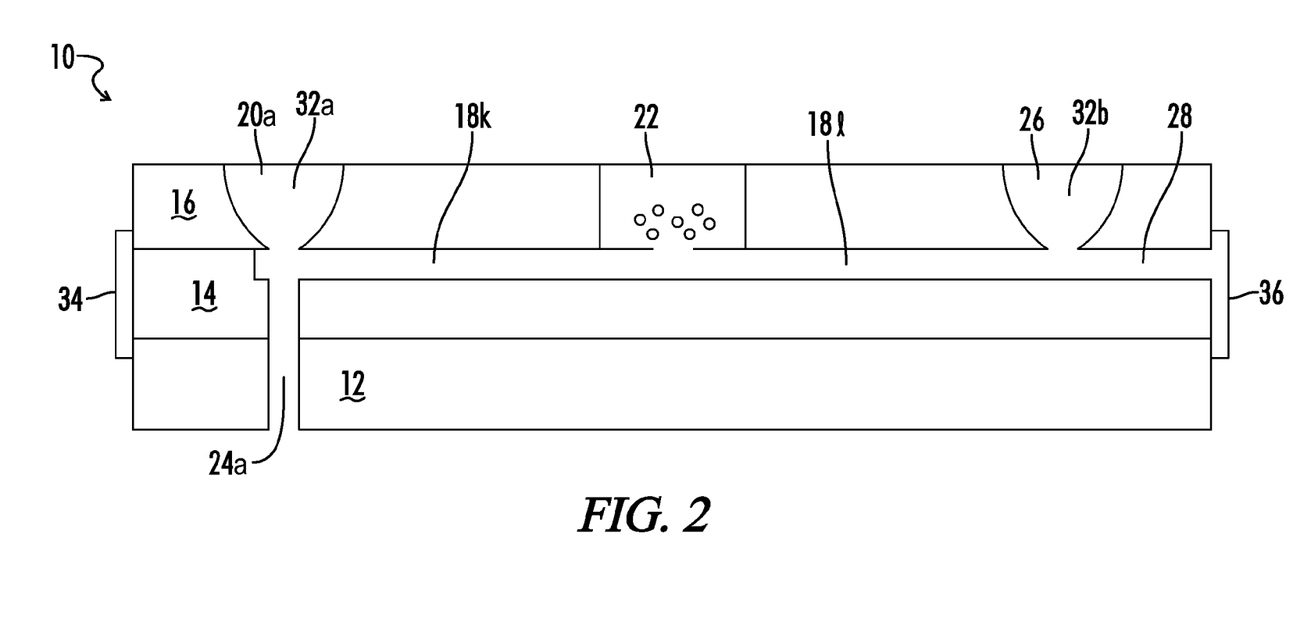
FIG. 2 depicts a side view of the substrate illustrated in FIG. 1

Each of the reagent ports 20a-20j and the exit port 26 include an electrical probe 32 which creates an electrical potential within the respective ports. Although a probe 32 is illustrated only for reagent port 20a, each of the reagent ports 20b-20j has a corresponding probe 32. All molecules and reagents necessary for oligonucleotide syntheses have a net charge which allows them to move within an electrical field. Selectively applying voltage to one of the reagent ports 20a-20j, while applying a voltage of the opposite charge to the exit port 26, creates a voltage differential on the substrate 10 between the two ports. This differential will cause the reagent to flow from the reagent ports 20a-20j, through the fluid channels 18a-18k and into the reaction chamber 22 for use in the synthesis reaction. The voltage differential will cause the reagent to flow out of the reaction chamber 22 and through fluid channel 18l. In one embodiment, the reactant may then exit the substrate 10 through exit port 26 or exit channel 28. This electroosmotic reagent flow occurs without the use of any pumps or valves. The substrate 10 may further include electrical connections 34 and 36, which facilitate the application of the voltage required to move the analytes over substrate 10. FIG. 2 illustrates a side view of substrate 10. In this embodiment, the top glass layer 16 of the substrate includes a reagent port 20a, a reaction chamber 22 and an exit port 26. In addition, the middle layer 14 of the glass substrate 10 includes etched fluid channels 18k-18l, exit channel 28 and tube 24a.

Figure 3:
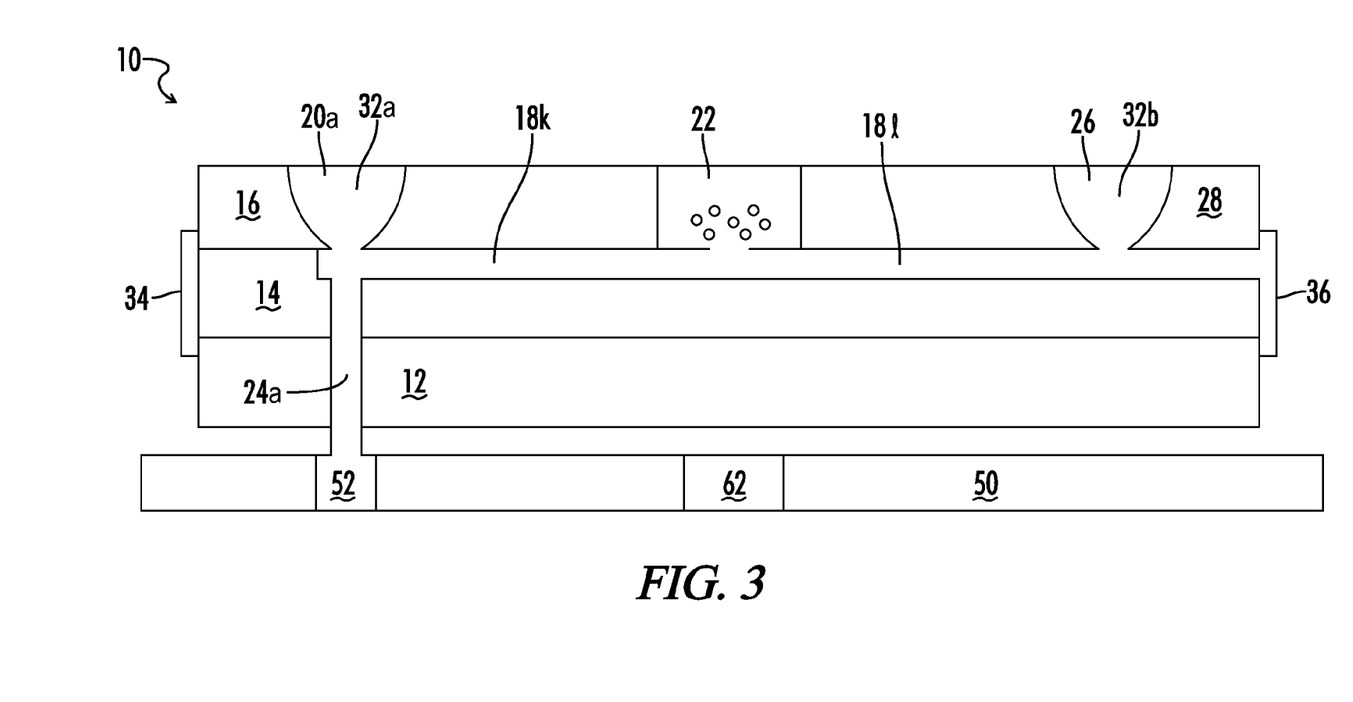
FIG. 3 depicts a side view of the substrate of FIG. 2 attached to a reagent cassette.

FIG. 3 illustrates the substrate 10 of FIG. 2 positioned above a reagent cassette 50. Reagent cassette 50 includes fluid wells 52 which hold the reagents necessary for oligonucleotide synthesis. Although only one well is illustrated in FIG. 2, the cassette 50 may contain a plurality of fluid wells 52, the number of fluid wells corresponding to the number of reagent ports 20a-20j (FIG. 1). As will be illustrated in more detail herein, the reagent plate snaps onto or is otherwise attached to the substrate 10 and positioned such that each fluid well 52 will lie directly below and correspond to each reagent port 20a-20j. This placement allows for specific synthesis reagents and analytes to be introduced into each reagent port 20a-20j.

The reagent cassette 50 further includes a magnet 62 positioned within the cassette 50 such that it contacts, or is placed very close to, the reaction chamber 22. As will be described in more detail herein after, the magnet 62 produces a magnetic field which attracts the paramagnetic solid support 30 (FIG. 1) contained within the reaction chamber 22. The magnetic field produced by magnet 62 creates a magnetic force which acts to hold the paramagnetic solid support 30 within the reaction chamber 22 and prevent its undesired movement out of the reaction chamber 22. In one embodiment, each of the reaction chambers 22 will be positioned near a corresponding magnet 62. In an additional embodiment, each reaction chamber 22 in the reagent cassette 22 will be positioned such that it is close proximity to a single magnet 62. In yet an additional embodiment, one magnet 62 may be moved within the reagent cassette 22 so that it may come into contact or is in close proximity to each of the reaction chamber 22.

Figure 4:
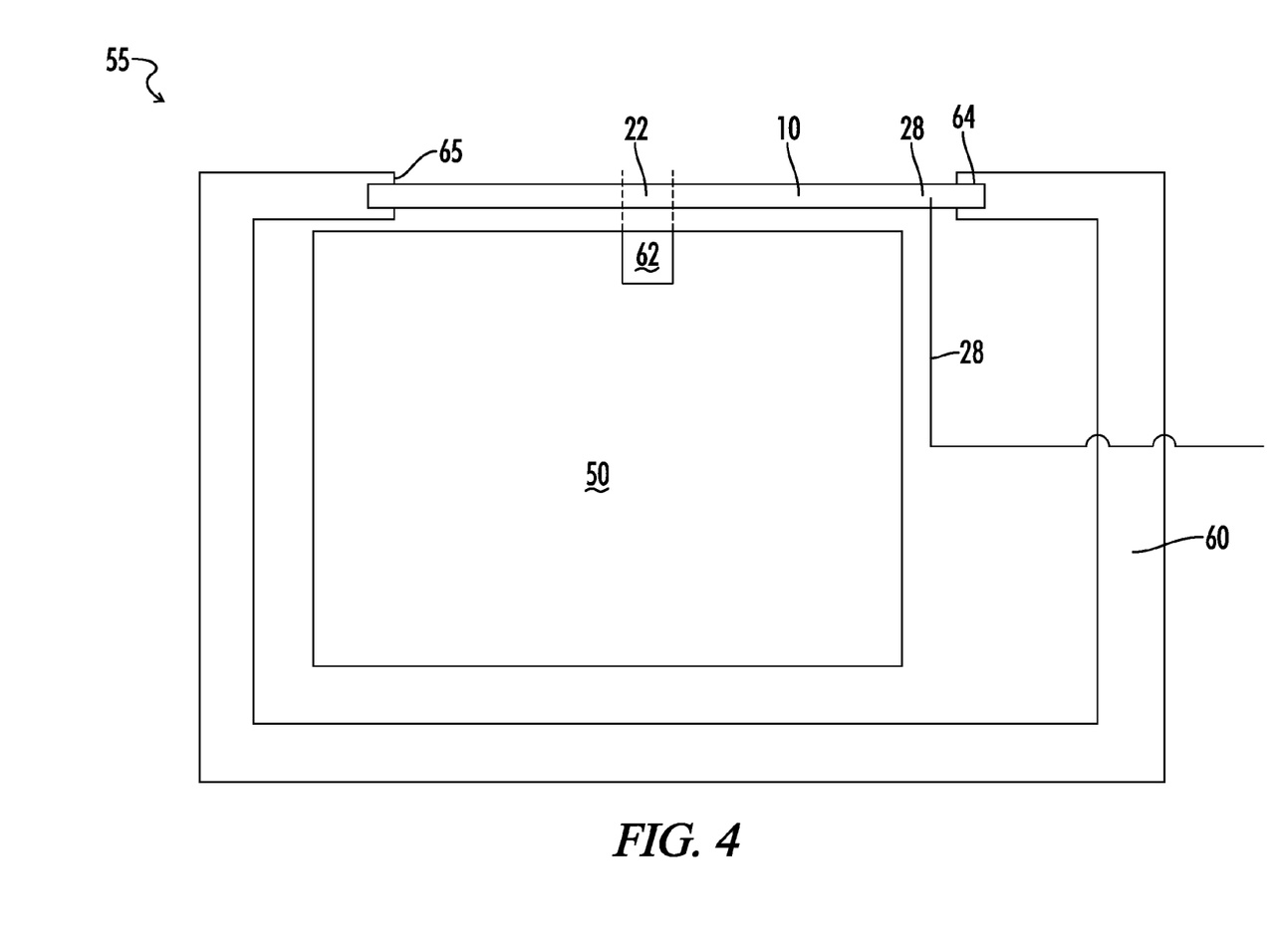
FIG. 4 depicts a side view of the substrate and cassette illustrated in FIG. 3 secured within a chassis.

FIG. 4 illustrates a side view of a reactor assembly 55 for the synthesis of oligonucleotides. In this embodiment, the substrate 10 and the reagent cassette 50 of FIG. 3 are positioned within a support chassis 60. In the embodiment illustrated in FIG. 4, the chassis 60 includes two attachment sites 64 and 65 which secure substrate 10. The attachment devices may take any form provided that act to secure the substrate 10 and prevent movement. Examples of such attachment devices 64 and 65 are clips and latches. The chassis 60 acts as an outer framework to secure the substrate 10 and cassette 50 during the synthesis reaction. In addition, the chassis 60 prevents movement of the substrate 10 and cassette to ensure proper alignment of the reagent ports 20a-20j and fluid wells 52 (FIG. 3). The chassis 60 may be constructed of a number of materials that provide the necessary support for the substrate 10. In one example the chassis 60 is made from a metal such as steel, but other materials are possible in other embodiments. The chassis 60 illustrated in FIG. 4 illustrates one substrate 10 and one cassette 50 confined within its interior. However, multiple substrates 10 may be positioned within the chassis 60. In one embodiment, chassis 60 may accommodate six substrates 10, positioned in a side-by side manner. In this orientation, 96 reaction chambers (6 substrates with 16 reaction chambers each) would be present for the production of 96 oligonucleotides.

Figure 5:
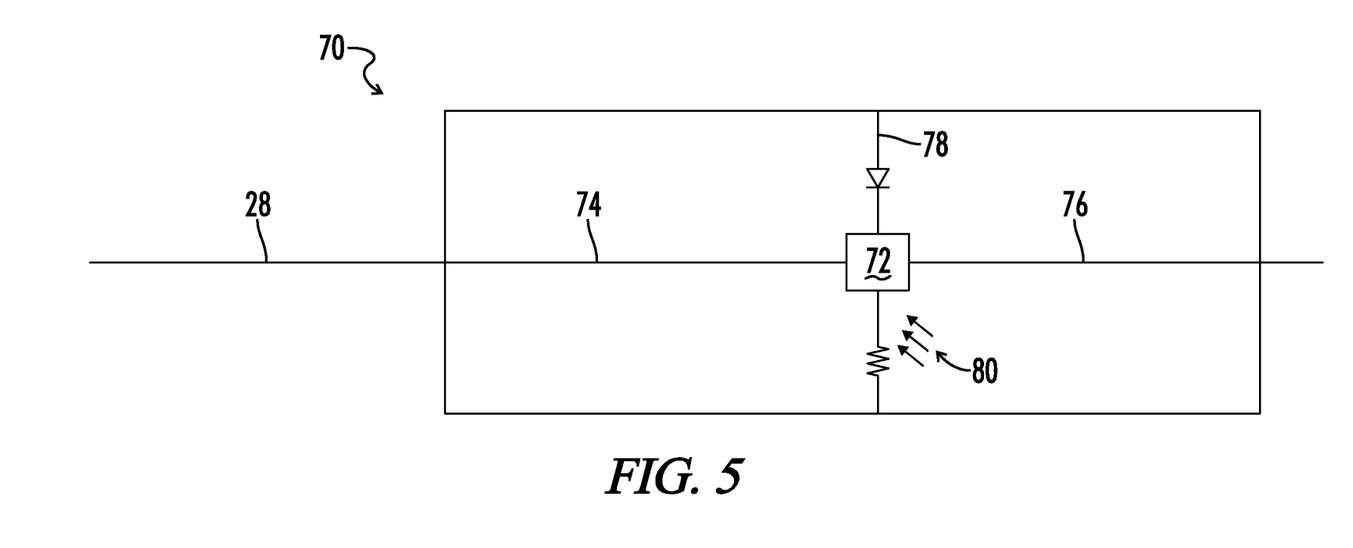
FIG. 5 depicts a side view illustrating an exemplary spectrophotometer in accordance with an embodiment of the disclosure.

In the embodiment illustrated in FIG. 4, synthesized oligonucleotides exit the substrate 10 via exit channel 28. The products may be collect and purified before use as will be known to one of skill in the art. Additionally, spectrophotometric analysis may be performed on the synthesis products to determine the concentration of synthesized oligonucleotides. FIG. 5 illustrates a spectrophotometer 70 for use in determining the concentration of synthesized oligonucleotides. In this embodiment, the oligonucleotide synthesis products exit the reaction assembly 55 via exit channel 28 (FIG. 4). The products then enter a spectrophotometer 70 through incoming channel 74. As will be known to one of skill in the art, the spectrophotometer 70 includes a cuvette 72 which holds the reaction products during analysis. UV source 80 directs light in the ultraviolet spectrum through cuvette 72 containing the products. The specific wavelength produced and directed by the UV source 80 will be selected based upon the type of synthesis products present in the cuvette (i.e., DNA, RNA, amino acid, etc.). Exiting UV light is then collected by a UV detector 78. As will be discussed in more detail herein, the concentration of synthesized products may be calculated based upon the amount of light absorbed by the contents of the cassette 72.

Figure 7:
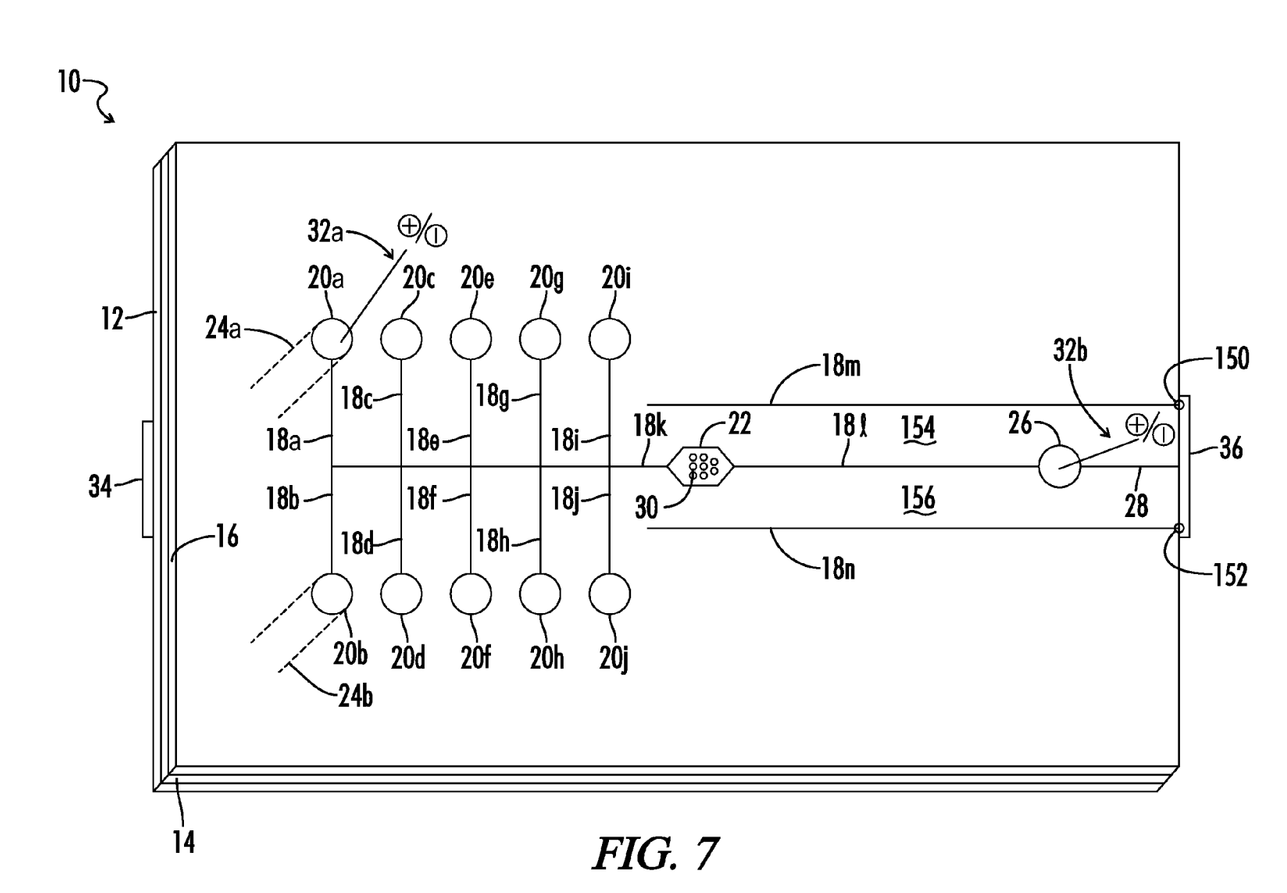
FIG. 7 depicts a front perspective view illustrating an exemplary reaction substrate with optical channels in accordance with an embodiment of the disclosure.

In an additional embodiment illustrated in FIG. 7, the optical spectroscopy is performed in-plane with the microfluidic substrate 10. In this embodiment, two channels 18m and 18n are positioned perpendicular to, but not connected to, microfluidic channel 18l. Optical fiber (not shown) is guided through the channels 18m and 18n. A small section of glass 154 and 156 is positioned between channels 18m and 18n to prevent fluidic contact. In addition, the sidewalls (not shown) of channels 18m and 18n are shaped in such a manner as to promote the optical path of the light passing from the fiber within channel 18m to the fiber within channel 18n. Elongated cylindrical holes 150 and 152 are positioned at the ends of channels 18m and 18n to allow for the placement of optical fiber (not shown) within the channels 18m and 18n. The optical fibers within channels 18m and 18n may be aligned and secured using conventional fiber optic positioning equipment (not shown) as is known to one with skill in the art.

Figure 6:
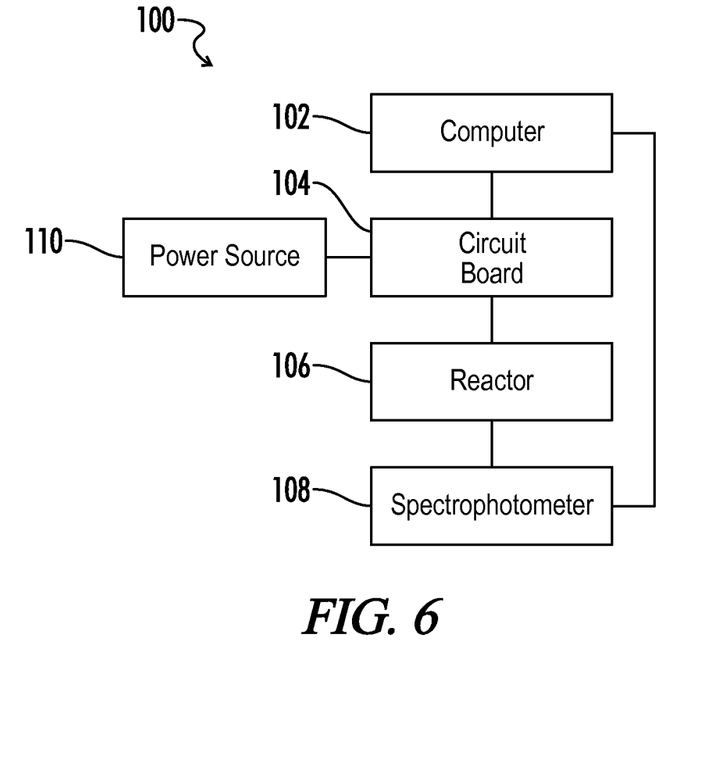
FIG. 6 depicts an exemplary oligonucleotide synthesis system in accordance with an embodiment of the disclosure.

In an additional embodiment, the present disclosure pertains to a system for the synthesis of oligonucleotides. Referring now to FIG. 6, synthesis system 100 includes a reactor assembly 106, described in detail above with reference to FIG. 4. The reactor assembly 106 includes at least one substrate 10 and a corresponding reagent cassette 50 contained within a protective chassis 60. In one embodiment, the system 100 utilizes at least one high voltage electroosmotic switching circuit 104 with a digital analog controller that may be utilized to regulate the power directed to at multiple individual fluid channels 18 (FIG. 1) in a single microfluidic substrate 10. The switching circuit 104 allows for very high voltages, for example in excess of 4000 V, with negligible amperage. In one embodiment, the system 100 also includes a controller 102 to direct the operation of the switching circuit 104. The electroosmotic flow characteristics of each of the reagents may be programed into the controller 102. The controller can be implemented in hardware, software, firmware or any combination thereof. In one embodiment, the controller 102 is implemented in a computer (e.g., a personal computer), with software running on the computer for controlling the switching circuit 104. A power supply 110 provides the needed power to the switching circuit 104. Exemplary power supplies 110 are known to those with skill in the art. In an additional embodiment, the power supply 110 may comprise a personal computer but other types of power supplies are possible. In this embodiment, the switching circuit 104 may receive power from a personal computer via a USB connection. In the embodiment illustrated in FIG. 6, system 100 further includes an optical spectrophotometer 108 which provided real-time optical measurement of synthesis products. In one embodiment, resulting optical readings from the spectrophotometer 108 may be provided to an analyzer 112, which may manipulate the data provided by the spectrophotometer 108 and present the data in a format chosen by the user. The analyzer can be implemented in hardware, software, firmware or any combination thereof. In one embodiment, the analyzer 112 is implemented in a computer, with software running on the computer.

In use, at least one reaction substrate 10 is placed within and secured to the chassis 60. A reagent cassette 50 is then preloaded with the reagents necessary for the desired synthesis reaction and secured below the substrate 10 so that each of the reagent ports 20a-20j on the substrate 10 are aligned with their corresponding fluid wells 52 located on the cassette 50. In addition, the magnet 62 of the cassette 50 will be positioned so that it is in contact with or very close to the reaction chamber 22 of the substrate 10. Once assembled, the reactor assembly 55 within the chassis 60 is connected to the switching circuit 104, which in turn is connected to the desired power supply.

The solid support material 30 is the prepared for use in the synthesis system 100. In one embodiment as described previously, the solid support comprises magnetic CPG with an iron core, although other types of paramagnetic solid support materials are possible in other embodiments. In one embodiment, the paramagnetic solid support material 30 is covered with a ceramic and coated with a compound appropriate for the type of synthesis reaction being employed. In one embodiment, the paramagnetic solid support 30 is then loaded into the reagent cassette 50. An electrical probe 32a is inserted into the reagent port 20a corresponding the fluid channel 18a in which the paramagnetic solid support 30 is loaded, while a second probe 32b is inserted in to the exit port 26. The controller 102 then signals the switching circuit 104 to apply a voltage (i.e., a positive voltage) to the probe 32a associated with the reagent port 18a while simultaneously applying the opposite voltage (i.e., a negative voltage) to the probe 32b associated with the exit port 26. The specific electroosmatic flow characteristics for each reagent utilized in the synthesis reaction have been programed into controller 102 so that the appropriate voltages may be applied to probes 32a and 32b.

The application of this voltage differential on substrate 10 and the production of an electroosmotic force causes the reagents to flow through the fluid channels of the system 100. As a result, the reagent in which the paramagnetic solid support material 30 is contained will begin to move with fluid channel 18a and 18k towards the reaction chamber 22. The magnet 62 placed in contact with or very close to the reaction chamber 22 will create a magnetic field such that a magnetic force holds the paramagnetic solid support material 30 on the interior wall of the reaction chamber 22 closest to the magnet 62. The magnetic force created by the magnet 62 is of great enough magnitude such that the paramagnetic solid support material 30 will not continue to flow through the microfluidic channels of the system 100. The use of the magnet 62 and paramagnetic solid support material 30 eliminates the need for filters or other materials currently used to hold the support material in the reaction chamber 22, thus greatly reducing the quantities of reagents and other materials needed in the synthesis reaction.

Prior to initiating the synthesis reaction the paramagnetic solid support material 30 must be treated so that it will have the ability to bind the growing oligonucleotide chain. This may be accomplished through the use of a linker. Linkers are molecules that can be attached to a solid support and to which the desired members of a library of chemical compounds may in turn be attached. When the construction of the library is complete, the linker allows clean separation of the target compounds from the solid support without harm to the compounds and preferably without damage to the support. To prevent undesired side reactions, all other functional groups present in nucleosides have to be rendered unreactive (protected) by attaching protecting groups. Upon the completion of the oligonucleotide chain assembly, all the protecting groups are removed to yield the desired oligonucleotides.

The chemical oligonucleotide synthesis process may then proceed on the treated immobilized paramagnetic solid support material 30. The presently disclosed methods utilize conventional chemical synthesis techniques with micro-scale quantities and therefore require no unconventional reagents or analytes. The oligonucleotide synthesis is carried out by a stepwise addition of nucleotide residues to the 5'-terminus of the growing oligonucleotide chain until the desired sequence is assembled. Each addition is referred to as a synthetic cycle and consists of four chemical reactions:

Step 1: De-blocking/Detritylation. The first base, which is attached to the solid support, is at first inactive because all the active sites have been blocked or protected. To add the next base, the DMT group protecting the 5'-hydroxyl group must be removed. This is done by adding a base, either dichloroacetic acid (DCA) or trichloroacetic acid in dichloromethane (TCA), to the solid support. The 5'-hydroxyl group is now the only reactive group on the base monomer. This ensures that the addition of the next base will only bind to that site. The solid support is then washed to remove any extra acid and by-products.

Step 2: Coupling. The next base monomer cannot be added until it has been activated. This is achieved by adding an activator to the base. The Activator cleaves off one of the groups protecting the phosphorus linkage. This base is then added to the solid support. The active 5'-hydroxyl group of the preceding base and the newly activated phosphorus bind to loosely join the two bases together. This forms an unstable phosphite linkage. The solid support is then washed to remove any extra tetrazole, unbound base and by-products.

Step 3: Capping. When the activated base is added to the solid support, some does not bind to the active 5'-hydroxyl site of the previous base. If this group is left unreacted in a step it is possible for it to react in later additions of different bases. This would result in an oligonucleotide with a deletion. To prevent this from occurring, the unbound, active 5'-hydroxyl group is capped with a protective group which subsequently prohibits that strand from growing again. This is done by adding acetic anhydride and N-methylimidazole to the reaction column. These compounds only react with the 5'-hydroxyl group. The base is capped by undergoing acetylation. The solid support is then washed to remove any extra acetic anhydride or N-methylimidazole.

Step 4: Oxidation. In step 2 the next desired base was added to the previous base, which resulted in an unstable phosphite linkage. To stabalize this linkage a solution of dilute iodine in water, pyridine, and tetrahydrofuran is added to the reaction column. The unstable phosphite linkage is oxidized to form a much more stable phosphate linkage.

Steps 1-4 are repeated for each nucleotide addition. After all bases have been added the oligonucletide must be cleaved from the solid paramagnetic support material 30 and deprotected before it can be effectively used. This is done by incubating the chain in an deprotection solution. All the protecting groups are now cleaved, including the cyanoethyl group, the heterocyclic protection groups. The DMT group on the 5' end of the oligo may have been retained for further purposes.

Each of the above steps requires one or more reagents to perform the necessary chemical reactions. The necessary reagents are preloaded into the fluid wells 52 of the reagent cassette 50. The controller 102 signals the switching circuit 104 to apply a voltage (i.e., a positive voltage) to the probe 32a associated with the reagent port 18b containing the needed reagent. The opposite voltage (i.e., a negative voltage) is simultaneously applied to the probe 32b associated with the exit port 26. This voltage differential on the solid support 10 directs the reagent to flow through the appropriate microfluidic channels. The specific electroosmatic flow characteristics for each reagent utilized in the synthesis reaction have been programed into controller 102 so that the appropriate voltages may be applied to probes 32a and 32b. As a result, the desired reagent will travel from the fluid well 52, through tube 24 and into the specific corresponding fluid channel 18a-18k until it comes into contact with the paramagnetic solid support material 30 in the reaction chamber 22. The reagent will facilitate the necessary chemical reaction as outlined in Steps 1-4 discussed above. The excess reagent will continue to flow through fluid channel 18l until it reaches exit port 26. In one embodiment, the substrate 10 will have an additional fluid channel (not shown) where fluid wastes will exit and be collected externally from the substrate 10. The controller 102 will continue to instruct the switching circuit 104 to sequentially apply voltage to the appropriate reagent ports 20a-20l to initiate flow of the needed reagent. The voltage differential created by the different voltages provides for the electroosmotic flow of all reagents necessary for the synthesis reaction through the microfluidic channels. This eliminates the need for pumps, valves or other moving parts which increase the cost or producing and maintaining of the system. In addition, the micro-scale quantities required for use in the described substrate 10 greatly reduce the amount of chemical reagents needed in the reaction.

In one embodiment, the presently disclosed oligonucleotide synthesis system 100 allows for the real-time monitoring of reaction products. In this embodiment, the system incorporates in-plane fiber optic spectroscopy to measure the yield of the oligonucleotide synthesis immediately after the reaction occurs. After each base has been added the synthesized strand must deprotected before it an additional base may be added. This is done by incubating the chain in an acidic solution. The released protecting group causes the solution in which it is residing to turn orange. The number of released protecting groups is directly proportional to the number of bases added to the synthesized chain. The intensity of the orange color in the solution may be measure spectrophotometrically to determine the concentration of synthesized oligonucleotide. This measurement may be made in real-time (i.e., after the addition of every base) or may be done after the addition of all the bases.

In this embodiment, the solution containing the cleaved, deprotected molecules moves through the microfluidic channel 18l, exit port 26 and exit channel 28 via the presence of the voltage differential. As explained above with reference to FIG. 5, the fluid then enters incoming spectrophotometer channel 74 where it is deposited in micro cuvette 72. The UV detector 78 measures the amount of transmitted UV light at a specified wavelength, as will be known to one of skill in the art. This information may be displayed for the user, for example on a screen located on the spectrophotometer. In an additional embodiment, the adsorption data may be analyzed by an analyzer 112 (FIG. 6) which then calculates the concentration of synthesized oligonucleotides and displays this information in a format determined by the user, as will be known to one of skill in the art. The synthesized oligonucleotide travels through microfluidic exit channel 76 where it is then collected.

After completion of the synthesis reaction, the magnet 62 may be removed from the substrate 10 to release the paramagnetic solid support 30. In one embodiment, this may be accomplished by removing the reaction cassette, which includes a magnet 50, and replacing it with a second cassette (not shown) which does not contain a magnet 62. This second cassette will include reagent ports containing chemicals for use in washing the substrate 10. The cleaning chemicals are propelled through the fluid channels 18a-18l, reaction chamber 22, exit port 26 and exit channel (FIGS. 1 and 2) using electroosmotic flow created with a voltage differential, as described above, thus removing the paramagnetic solid support 30. With the exception of the paramagnetic solid support 30, all of the components utilized in system 100 may be cleaned and reused in subsequent synthesis reactions. The system 100 may be utilized for a variety of chemical synthesis reactions by determining the electroosmotic flow properties of the reagents used in each process.

The presently described microfluidic synthesis systems and methods produce approximately 500 pmol of a specific oligonucleotide in approximately six to eight minutes. The chemical synthesis is achieved within a reusable, fully transparent glass micro-reactor which is chemically resistant to the chemical reagents used in the described methods. The micro-reactor is stable over a large temperature range. The microfluidic channels greatly reduce the volume of chemical reagents used in the synthesis reactions. The present systems and methods reduce the quantity of the required starting materials and chemical reagents beyond what it currently achievable. In addition, the reactors allow for the production of pico-scale quantities of product, reducing waste and costs. As an example, current production schemes are optimized for the production of 40,000 to 1,000,000 pmol (40 nmol to 1 umol respectively) oligos per synthesis reaction. However, the vast majority of end-use processes require a single reaction of 5-10 pmol of product, with the remainder of the material discarded as waste.

In addition, the currently disclosed systems and methods require no filters, thus drastically reducing the size of the reaction chamber. In addition, the electroosmotic movement of the reagents through microfluidic channels requires no pumps, valves or other moving parts, thus reducing the operating costs of the system. The systems and methods are applicable to the synthesis of oligonucleotides required for the synthesis short chain DNA, complex transmembrane proteins, site specific proteins, and even user generate proteins not otherwise found in nature. The reduced volume of this reactor allows the user to reduce waste, improve reaction synthesis times, and decrease the cost required to perform enzymatic protein research.

Now, therefore, the following is claimed:

1. An apparatus for synthesizing a molecule, comprising:
   a reaction substrate having at least one reaction chamber and at least one microfluidic channel for transferring a reagent to the reaction chamber;
   a reagent cassette coupled to the substrate, the reagent cassette having at least one reagent port for transferring the reagent from the cassette to the microfluidic channel;
   a power supply configured to apply a voltage differential, wherein the voltage differential is sufficient for generating an electroosmotic force to cause the reagent to flow from the cassette through the microfluidic channel;
   a paramagnetic solid support in contact with an interior wall of the reaction chamber, the paramagnetic solid support attached to a material for reacting with the reagent in the reaction chamber;
   a magnet positioned to hold the paramagnetic solid support in contact with the interior wall of the reaction chamber by a magnetic field generated by the magnet while the reagent is flowing through the reaction chamber;
   a first optical fiber passing through the reaction substrate; and
   a second optical fiber passing through the reaction substrate, wherein the first optical fiber and the second optical fiber are positioned on opposite sides of the reaction chamber such that an optical path passes from the first optical fiber through the reaction chamber to the second optical fiber for permitting real-time optical spectroscopy of at least one product within the reaction chamber, wherein each of the first optical fiber and the second optical fiber are separated from the reaction chamber by a section of the reaction substrate wherein the optical path is perpendicular to a direction of flow of the reagent in the reaction chamber.

2. The apparatus of claim 1, further comprising a spectrophotometer positioned near the microfluidic channel.

3. The apparatus of claim 1, wherein the reaction substrate comprises photodefinable glass.

4. The apparatus of claim 1, further comprising a plurality of reaction substrates.

5. The apparatus of claim 1, wherein the reaction substrate comprises a plurality of reaction chambers.

6. The apparatus of claim 1, wherein the paramagnetic solid support comprises paramagnetic controlled pore glass (CPG).

7. The apparatus of claim 1, further comprising a switching circuit for controlling the voltage differential.

8. The apparatus of claim 7, further comprising a controller for directing the operation of the switching circuit.

9. A method of synthesizing a molecule, comprising:
   providing a reaction substrate having at least one reaction chamber and at least one microfluidic channel;
   causing a reagent to flow from a reagent cassette through the microfluidic channel to the reaction chamber, wherein the causing comprises generating an electroosmotic force sufficient for moving the reagent from the cassette through the microfluidic channel to the reaction chamber;
   applying a magnetic field to a paramagnetic solid support located within the reaction chamber, the paramagnetic solid support attached to a material for reacting with the reagent;
   holding the paramagnetic solid support in contact with an interior wall of the reaction chamber while the reagent is flowing through the reaction chamber with a magnetic force generated by the applied magnetic field, wherein the material reacts with the reagent in the reaction chamber thereby forming at least one product;
   passing light from a first optical fiber positioned in the reaction substrate through the reaction chamber to a second optical fiber positioned in the reaction substrate during reaction of the reagent with the material, wherein each of the first optical fiber and the second optical fiber are separated from the reaction chamber by a section of the reaction substrate wherein the optical path is perpendicular to a direction of flow of the reagent in the reaction chamber; and performing real-time optical spectroscopy of the product during the reaction of the reagent with the material.

10. The method of claim 9, further comprising taking a spectrophotometric measurement of the reagent with a spectrophotometer.

11. The method of claim 9, wherein the generating comprises applying a voltage differential to the substrate.

12. The method of claim 11, further comprising controlling the voltage differential with a switching circuit.

13. The method of claim 12, further comprising directing the operation of the switching circuit with a controller.

14. The method of claim 9, further comprising the step of causing a second reagent to flow from the cassette through the microfluidic channel.

15. The method of claim 14, wherein the causing comprises generating an electroosmotic force sufficient for moving the second reagent from the cassette through the microfluidic channel to the reaction chamber.

16. The method of claim 15, wherein the generating comprises applying a voltage differential to the substrate.

17. The method of claim 11, further comprising calculating the yield of the synthesized molecule from the spectrophotometric measurement of the reagent.

18. The method of claim 9, further comprising:
removing the magnetic field from paramagnetic solid support within the reaction chamber; and
causing the reagent and the paramagnetic solid support to flow within the microfluidic channel.

19. A method of synthesizing a molecule, comprising:
providing a reaction substrate having at least one reaction chamber and at least one microfluidic channel;
causing a reagent to flow from a reagent cassette through the microfluidic channel to the reaction chamber, wherein the causing comprises generating an electroosmotic force sufficient for moving the reagent from the cassette through the microfluidic channel to the reaction chamber;
loading a paramagnetic solid support into the reagent cassette;
moving the paramagnetic solid support with the reagent through the microfluidic channel toward the reaction chamber;
applying a magnetic field to the paramagnetic solid support located within the reaction chamber, the paramagnetic solid support attached to a material for reacting with the reagent;
holding the paramagnetic solid support in contact with an interior wall of the reaction chamber while the reagent is flowing through the reaction chamber with a magnetic force generated by the applied magnetic field, wherein the material reacts with the reagent in the reaction chamber thereby forming at least one product;
passing light from a first optical fiber positioned in the reaction substrate through the reaction chamber to a second optical fiber positioned in the reaction substrate during reaction of the reagent with the material; and
performing real-time optical spectroscopy of the product during the reaction of the reagent with the material.

20. The method of claim 9, further comprising generating the magnetic field with a magnet positioned in the reagent cassette.

21. The apparatus of claim 1, wherein the magnet is positioned in the reagent cassette.

22. The apparatus of claim 1, wherein the paramagnetic solid support comprises magnetic controlled pore glass and an iron core.

23. The apparatus of claim 1, wherein the material for reacting with the reagent comprises a linker molecule, and a synthesized molecule is attached to the linker molecule.

* * * * *